United States Patent [19]

Davies et al.

[11] 4,077,994

[45] Mar. 7, 1978

[54] SILOXANES

[75] Inventors: William Grenville Davies, Longfield; Howard Victor Andrew Beedle, Swanscombe, both of England

[73] Assignee: The Associated Portland Cement Manufacturers Limited, London, England

[21] Appl. No.: 613,864

[22] Filed: Sep. 16, 1975

[30] Foreign Application Priority Data

Sep. 24, 1974 United Kingdom ............... 41495/74

[51] Int. Cl.$^2$ ............................................... C07F 7/08
[52] U.S. Cl. ..................... 260/448.2 E; 260/448.2 H; 260/448.2 Q; 260/448.2 R
[58] Field of Search .................. 260/448.2 E; 423/336

[56] References Cited

U.S. PATENT DOCUMENTS

| 3,297,632 | 1/1967 | Wu | 260/448.2 E UX |
| 3,310,526 | 3/1967 | Sporck | 260/448.2 E UX |
| 3,398,173 | 8/1968 | Goossens | 260/448.2 E UX |
| 3,590,064 | 6/1971 | Lacefield | 260/448.2 E |
| 3,694,405 | 9/1972 | Litteral | 260/448.2 E X |
| 3,792,072 | 2/1974 | Lewis | 260/448.2 E |
| 3,842,110 | 10/1974 | Razzano | 260/448.2 E |

OTHER PUBLICATIONS

Currell et al., "Formation of Polyorganosiloxanes from Silicate Minerals" in Nature Physical Science, vol. 236, p. 108, 4/1972.

Pierce, "Silylation of Organic Compounds," pp. 7 & 8, 1968.

Primary Examiner—Paul F. Shaver
Attorney, Agent, or Firm—Diller, Brown, Ramik & Wight

[57] ABSTRACT

A method of producing a cyclic siloxane by silylating a cyclic silicate with a chlorosilane characterized by reacting the silicate with the chlorosilane in a ketone which is a solvent for the chlorosilane, in the presence of a minor molar proportion with respect to the chlorosilane, of a hydroxy compound soluble in the ketone, and purifying the resulting reaction mixture to recover the cyclic siloxane therefrom.

12 Claims, No Drawings

SILOXANES

The present invention relates to cyclic siloxanes obtainable from cyclic silicates, especially from calcium silicate and referred to herein as intermediates, which are capable of polymerisation to provide a new class of siloxane polymers.

The preferred cyclic siloxanes with which the invention is concerned correspond to the general formula (I):

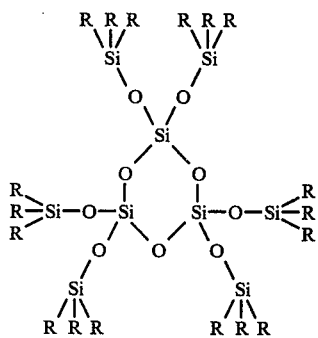

wherein the groups R may be the same as each other or different and are hydrogen or substituted or hydrocarbyl, i.e., unsubstituted alkyl, aryl, alkaryl or alkenyl groups, the substituents being for instance halo, cyano or amino groups.

A particular example of an intermediate of the general formula I is hexa(trimethylsiloxy)cyclotrisiloxane, referred to herein as intermediate II. Intermediate II is the compound of formula I in which every group R is methyl.

The invention will be particularly described, for convenience and clarity, by reference to the intermediate II, hexa(trimethylsiloxy)cyclotrisiloxane, but it will be appreciated that the methods of the invention are readily applicable to other cyclic silicates.

It is an object of the invention to provide novel cyclic siloxane intermediates from which a range of useful siloxane polymers may be produced by polymerization.

It is another object of the invention to provide a novel class of linear polymeric siloxanes and a method of producing them particularly from calcium silicate.

It is a further object of the invention to produce novel polymeric siloxanes in a good yield and in a readily controlled manner, from an economically available material.

It is known from C. W. Lentz (Inorganic Chemistry 1964, 3, 574) to silylate certain silicate minerals by reacting the mineral with concentrated hydrochloric acid in the presence of hexamethyldisiloxane, isopropanol and ice. The cations are slowly leached out from the mineral and trimethylsilyl end-blocked silicates are yielded, having the silicate structure of the particular mineral. In the case of the ring-structured calcium aluminosilicate laumontite, the products account for 80.9 percent of the silicon in the form of octa(trimethylsiloxy)cyclotetrasiloxane. The trimethylsilylation reagent is presumed to be trimethylchlorosilane or trimethylsilanol, both of which are derived by interaction of the hexamethyldisiloxane and the hydrochloric acid.

In a more direct attempted route to silylated silicate, J. Gotz and C. R. Masson (Journal of the Chemical Society A., 1970, 2683) replaced the hydrochloric acid and ice of the Lentz method by trimethylchlorosilane itself. They investigated the role of the isopropanol and of water, in the reaction with a ring-structured silicate.

Ring-structured silicates are not widely abundant, and the systems which are thought to exist as discrete rings, as opposed to linked rings constituting a framework silicate, are those with the anions $(SiO_3)_3^{-6}$, $(SiO_3)_4^{-8}$, and $(SiO_3)_6^{-12}$, the first of these being the rarest.

The present invention is concerned with a process of solvent treatment in which cations are removed from a silicate having a structure of discrete rings, but the structural principle of the silicate, i.e., the cyclic structure, persists in the polymerisable intermediate product obtained. The trimethylsilylated silicate minerals are of interest as potential starting materials for useful siloxane polymers. The prior literature, does not, however, disclose the type of intermediate produced in the preferred embodiment of this invention, nor the particular use of calcium silicate in the initial silylation.

The invention is described in terms of cyclic siloxanes obtained from a particular form of calcium silicate, but it is contemplated that not only other forms of calcium silicate but also silicates of other metals, are amenable to analogous treatment to yield useful polymerisable intermediates retaining some skeletal character of the silicate precursor material. Such variations of the process described fall within the scope of the invention.

It has long been known to polymerize cyclic diorganosiloxanes e.g., in the presence of basic catalysts, to produce high molecular weight linear siloxane polymers. The course by which the polymerization of such cyclic siloxanes has been believed to proceed involves the stepwise addition of cyclic siloxane units to a silanolate active centre, one result of which is a broad spectrum of molecular weights in the polymer products. U.S. Pat. No. 3,481,898 describes the polymerization of such cyclic siloxanes to produce organopolysiloxanes having a narrow molecular weight distribution.

According to the invention we provide a method of producing a cyclic siloxane by silylating a cyclic silicate with a chlorosilane characterised by reacting the silicate with the chlorosilane in a liquid organic reaction medium, preferably a solvent such as a ketone, in the presence of a minor molar proportion with respect to the chlorosilane, of a hydroxy compound soluble in the reaction medium, and purifying the resulting reaction mixture to recover the cyclic siloxane therefrom.

According to the present invention we provide in particular a method of producing a compound of the formula I which comprises silylating pseudo wollastonite with a chlorosilane, preferably a triorganochlorosilane, by reacting the pseudo wollastonite with the chlorosilane in the abovementioned solvent and in the presence of the hydroxy compound, if desired at slightly elevated temperature, and purifying the resulting reaction mixture.

If desired the reaction may be performed at ambient temperature or at elevated temperature.

When the chlorosilane is trimethylchlorosilane, the method leads to the production of compound II.

The reaction medium used is preferably a solvent such as acetone, methylpropyl ketone or cyclohexanone but these are only representative of the class of solvents which may be used in this context. The hydroxy compound may for instance be water, an alcohol or an ether alcohol or a mixture of these; in general a very large range of organic hydroxy compounds may serve the purpose of the invention as long as they enter into the liquid phase with the ketone by solution, possible with melting.

The minor proportion of hydroxy compound is preferably from 0.01 to 25, more preferably from 0.1 to 16, mol percent based on the chlorosilane. Pressure may be applied if it is desired to operate at a temperature at which a liquid component would otherwise evaporate off.

A preferred reaction medium is acetone with tertiary butanol as the hydroxy compound.

The invention further provides a process of preparing linear siloxane polymers of the formula (III):

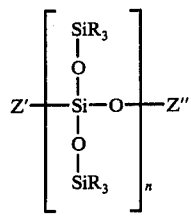

wherein the six groups R are as defined in the foregoing description in relation to formula I, $n$ is an integer, Z' is an end group, e.g., $(CH_3)_3Si—O—$ depending on the polymerisation catalyst, and Z'' is an end group depending on the reagent used to terminate polymerization e.g., hydrogen or $—Si(CH_3)_3$, which process comprises polymerising an intermediate of the formula I, and especially of the formula II, in the presence of a polymerization catalyst, preferably a basic catalyst.

Examples of the groups R, are methyl, ethyl, propyl, etc., trifluoropropyl, cyanoethyl, aminoethyl, phenyl, toluyl, allyl and vinyl. In the case of substituted alkyl groups there are preferably at least two carbon atoms in the chain between the silicon atom and the substituent.

The invention also embraces the production of random, block or graft copolymers by carrying out the aforesaid polymerisation process in an appropriate manner together with a further siloxane monomer, or with an organic monomer.

The basic catalyst can in general be any which is known in the art for polymerising cyclic siloxanes, for instance as mentioned in U.S. Pat. No. 3,481,898, lithium hydrocarbon compounds such as lithium butyl being preferred. The catalyst is employed in proportions usually employed in the art for the polymerization of cyclic organosilicon compounds. The actual proportion for any given case will depend, for example, on the nature of the catalyst. In general, however, proportions of catalyst within the range from 0.01 to 5 percent by weight, based on the weight of the cyclic material, will suffice, although proportions outside this range can be used if desired.

The polymerisation reaction is brought about by contacting the cyclic siloxane and the catalyst at the desired temperature for liquid phase operation. The polymerization process is conveniently performed in the presence of an organic solvent such as toluene or xylene and preferably in conjunction with a polar co-solvent such as tetrahydrofuran, dimethylformamide, dimethoxyethane and dimethylsulphoxide.

The molecular weight and distribution of molecular weight in the polymer product may be controlled by selection of the reaction conditions according to known principles to provide product of desired properties. Polysiloxanes are well known to have a range of distinctive properties and uses, to which the products of the present invention contribute.

Pseudo wollastonite is a metastable calcium silicate ($CaSiO_3$) formed when calcium silicate is heated above an inversion temperature of approximately 1200° C. Pseudo wollastonite may be prepared by three routes: (1) heating natural wollastonite above the inversion temperature of about 1200° C; (2) directly combining silica and calcium carbonate in equimolar amounts in a furnace about 1200° C; and (3) preparing pure calcium silicate synthetically by precipitation from sodium silicate and calcium chloride and heating the product above 1200° C. Natural wollastonite or its constituents may therefore be employed as starting materials in the process of the invention, being converted into pseudo wollastonite in an initial stage.

For the purpose of the illustrative Examples herein, the third method referred to above was used to obtain pseudo wollastonite as follows:

Aqueous solutions were prepared of sodium metasilicate, $Na_2SiO_3.5H_2O$, (424 g in 900 mls) and commercial calcium chloride flake, 70 percent $CaCl_2$ (317 g in 900 mls). The solutions were filtered and simultaneously poured slowly into a vessel containing 1 liter of water which was stirred throughout the process. The precipitate of calcium silicate formed was filtered, washed with five 1 liter volumes of distilled water, and dried at 105° C. The dried calcium silicate was heated in a muffle furnance for 4 hours at 1300° C., cooled and ground to a particle size of less than 45 microns. The product was analysed by X-ray diffraction and Infra Red Spectroscopy and shown to be pseudo-wollastonite.

The following Examples are given for the purpose of illustrating the invention. Examples I to V describe the preparation of intermediate compound II and Examples VI and VII illustrate the polymerisation process.

EXAMPLE I

| Materials: | |
|---|---|
| tertiary butanol | 2.05 g (0.05 moles on $(CH_3)_3$ SiCl) |
| acetone | 186 mls. |
| trimethylchlorosilane | 60 g |
| pseudo wollastonite below 45 microns | 60 g |

Experimental

The powdered pseudo wollastonite was added to the acetone/butanol trimethylchlorosilane mixture and the reactants refluxed for 3½ hours at 53.5° C. The reaction products were filtered and the residue was washed with acetone, the washings being added to the filtrate.

Sodium bicarbonate was added to the filtrate to neutralise any free hydrochloric acid and the filtrate was dried over anhydrous sodium sulphate. The solution of the product was then filtered and evaporated to dryness on a water bath leaving a crystalline solid.

The crude crystalline product was purified by recrystallization from methanol and then finally from a methanol/petroleum ether mixture. The pure hexa(trimethylsiloxy)cyclotrisiloxane obtained had a melting point of 103° C.

The inorganic residue was dried at 105° C. and weighed before washing with water and Tergitol Anionic 4 surfactant (Union Carbide), drying and reweighing.

| Yields | | | |
|---|---|---|---|
| (1) Siloxane Products: | | | |
| total yield (per cent W/W on (CH$_3$)$_3$SiCl) | | 69.4 | per cent |
| purity (per cent W/W filtered crystalline siloxane) | | 100.0 | per cent |
| (2) Residue | | | |
| total residue | | 65.0 | g |
| insoluble residue | | 35.8 | g |
| water soluble residue (CaCl$_2$) | | 29.2 | g |

Analysis

Infra-red analysis of the product indicated a methylsilylated siloxane with absorption bands at 1040 - 1060 cm$^{-1}$, 550 and 785 cm$^{-1}$, considered to be associated with the cyclic Si-O bond. Mass spectrometry confirmed that the purified and recrystallized material had a molecular weight of 666 with a probable formula of compound II.

The water-soluble residue confirmed that greater than 95 percent of the desired reaction had occurred. Infra-red analysis of the insoluble residue demonstrated that it was predominantly unreacted pseudo wollastonite together with a small proportion of partially silylated wollastonite.

EXAMPLE II

| Materials: | | |
|---|---|---|
| acetone | 80 | mls |
| distilled water | 0.4 | g |
| trimethylchlorosilane | 30.0 | g |
| pseudo wollastonite below 45 microns | 10.0 | g |

Experimental

The powdered pseudo wollastonite was added to the acetone/water/trimethylchlorosilane mixture and the mixture shaken at room temperature for 17 hours. The reaction products were filtered and the residue washed with acetone, the washings being added to the filtrate.

The filtrate was poured into a large volume of water, and the oily layer which formed was removed. The aqueous layer was washed several times with diethyl ether, and the washings added to the oily layer. The oil/ether mixture was dried over anhydrous sodium sulphate and the ether evaporated, leaving a mixture of a crystalline material and an oil. The crystalline material was separated from the oil by recrystallisation from methanol.

The residue was treated as in Example I.

TABLE 1

| Yields: | | | |
|---|---|---|---|
| (1) Siloxane Products | | | |
| Siloxane product | yield(g) | percent Yield on (CH$_3$)$_3$SiCl | percent Yield on wollastonite |
| Crystalline siloxane and oil | 8.4 g | 27.4 | 43.9 |
| Recrystallised material | 5.0 g | 16.3 | 26.1 |
| (2) Residue | | | |
| total residue | | 13.3 | g |
| insoluble residue | | 3.0 | g |
| water soluble residue (CaCl$_2$) | | 10.3 | g |

Analysis

The crude siloxane product was shown by chromatographic analysis to consist of a mixture of low and high molecular weight products, while the recrystallized material was a pure low molecular weight product, which was shown by analysis to be hexa(trimethylsiloxy)cyclotrisiloxane.

The insoluble residue (3 g) was shown by infra-red analysis to be silica.

The amount of calcium chloride produced suggested that total cation leaching had taken place. However, the residue of silica showed that the silicate structure had been partially destroyed by hydrochloric acid produced in the reaction which accounted for the low yield of siloxane products (43.9 percent on wollastonite).

EXAMPLE III

In order to minimise the unwanted by-products of Example II, diethyl ether was added to the system to combine with any free hydrogen chloride formed by reaction between trimethylchlorosilane and water.

| Materials: | | |
|---|---|---|
| acetone | 60 | mls |
| distilled water | 0.4 | g |
| trimethylchlorosilane | 30.0 | g |
| pseudo wollastonite below 45 microns | 10.0 | g |
| diethyl ether | 20 | mls |

Experimental

The experimental procedure followed that of Example I except that the reactants were refluxed for 3 hours at 47° to 48° C.

TABLE 2

| Yields: | | | |
|---|---|---|---|
| (1) Siloxane Products: | | | |
| Product | Yield(g) | percent yield on (CH$_3$)$_3$SiCl | percent yield on wollastonite |
| Crystalline siloxane and oil | 6.8 | 22.2 | 35.5 |
| (2) Residue | | | |
| total residue | 11.5 | g | |
| insoluble residue (compare page 13, lines 7 & 8) | 5.4 | g | |
| water soluble residue (CaCl$_2$) | 6.1 | g | |

Analysis

Infra-red and chromatographic analysis of the siloxane products confirmed that they were a mixture of methyl silylated siloxanes with a high proportion of hexa(trimethylsiloxy)cyclotrisiloxane as in Example II.

The insoluble residue was shown by infra-red analysis to be a mixture of unreacted pseudo wollastonite and of partially silylated wollastonite.

Infra-red analysis also showed that silica was not produced in this reaction.

The low yields of siloxane products and calcium chloride show that the reaction is not complete after the 3 hours at 48° C.

Whilst yields were similar to Example II no silica was formed but the oil by-product was still present.

EXAMPLE IV

Example IV shows the use of an alcohol as the hydroxy compound together with an ether.

| Materials: | |
|---|---|
| alcohol | see Table 3 for type and concentration |
| diethyl ether | 26 ml |
| trimethylchlorosilane | 60 g |
| acetone | 186 ml |
| pseudo wollastonite below 45 microns | 60 g |

Experimental

The experimental procedure followed that of Example I.

See Table 3 for reaction times and reflux temperatures.

TABLE 3

| | Methanol | Tertiary butanol | Tertiary butanol |
|---|---|---|---|
| alcohol weight (g) | 1.58 | 3.66 | 2.05 |
| concentration (moles on (CH₃)₃ SiCl) | 0.09 | 0.09 | 0.05 |
| reaction temperature (° C) | 51–53 | 51–53 | 51–53 |
| Reaction time (hr) | 3 | 5 | 14 |
| Siloxane products | | | |
| total yield (per cent W/W on (CH₃)₃ SiCl)) | 59.3 | 61.4 | 63.8 |
| purity (per cent W/W filtered crystalline siloxane) | 64.5 | 75.3 | 100.0 |
| per cent yield filtered crystalline siloxane (on (CH₃)₃SiCl)) | 38.3 | 46.3 | 63.8 |
| Residues | | | |
| total weight (g) | 66.7 | 66.2 | 65.5 |
| insoluble residue (g) | 36.5 | 37.5 | 37.2 |
| calcium chloride (g) | 30.2 | 28.7 | 28.3 |

The results of Example IV show that optimum results depend on concentration. The yield of cyclic crystalline siloxane increased with decreasing alcohol concentration, but the reaction rate decreased.

The amount of calcium chloride produced was 92 to 98 percent theoretical on the weight of trimethylchlorosilane used.

It will be noted that negligible amounts of the oil by-product were formed in the use of tertiary butanol with an ether in Example IV. Example I however, using t-butanol at low concentrations without ether, gave a more rapid reaction and produced pure intermediate (II) in good yields.

EXAMPLE V

In this Example an ether alcohol is used instead of the ether and alcohol of Example IV.

| Materials: | |
|---|---|
| butyl dioxitol | see Table 4 for concentration |
| trimethylchlorosilane | 60 g |
| acetone | 186 ml |
| pseudo wollastonite below 45 microns | 60 g |

Experimental

The experimental procedure followed was that of Example I.

See Table 4 for reaction times and reflux temperatures.

TABLE 4

| | 1 | 2 | 3 |
|---|---|---|---|
| Butyl Dioxitol weight (g) | 8.96 | 4.48 | 2.24 |
| concentration (moles on CH₃)₃ SiCl) | 0.10 | 0.05 | 0.025 |
| reaction temperature (° C) | 57.5 | 55–56.5 | 54–55 |
| reaction time (hrs) | 4½ | 5½ | 19 |
| Siloxane products | | | |
| total yield (percent W/W on (CH₃)₃ SiCl)) | 78.2 | 74.3 | 69.9 |
| purity (percent W/W filtered crystalline siloxane) | 37.5 | 45.4 | 71.6 |
| percent yield filtered crystalline siloxane on (CH₃)₃ SiCl) | 29.3 | 33.7 | 50.0 |
| Residues | | | |
| total weight (g) | 64.3 | 65.0 | 65.6 |
| insoluble residue (g) | 34.6 | 36.0 | 36.5 |
| calcium chloride (g) | 29.7 | 29.0 | 29.1 |

The foregoing Examples show that pseudo wollastonite may be reacted directly with chlorosilanes to give an intermediate of formula (I) in high yields. The main differences from previously reported comparable syntheses are:

1. The use of a ketone such as acetone as the solvent medium for the reaction.
2. The use of trimethylchlorosilane as the silylating agent and not hexamethyldisiloxane.
3. The use of only a small proportion of water, if any.
4. The use of an alcohol in preference to water.
5. The possible use of ether-alcohols or other hydroxy compounds.
6. The use of elevated temperature. All previous comparable reaction schemes tend to be used at 0° C. in ice or at ambient temperatures.

In the more general sense, we provide a silylation which, in comparison with the known art, has the following particular advantageous features: it does not employ hydrochloric acid as such, which would lead to a variety of unwanted side products by breakdown of the siloxane chain; it employs solvents capable of effectively wetting the silicate surface, the phases present then being only two, with consequently more favourable reaction conditions; especially when synthetic pseudo wollastonite is used, a pure reactive monomer product is isolated whereby the course of polymerisation and molecular weight of the eventual polymer is more amenable to control; and reaction conditions are formulated for high yield.

EXAMPLE VI

Polymerisation of hexa(trimethylsiloxy)cyclotrisiloxane.

| Materials: | |
|---|---|
| Hexa(trimethylsiloxy)cyclotrisiloxane (recrystallised from 40/60 petroleum ether and methanol) | 21.0 g |
| Potassium silanolate catalyst solution (1.25M) | 0.2 mls |
| Dimethyl formamide/toluene (ten per cent v/v) | 5.0 mls |

Experimental

The catalyst solution was prepared from octa-methyl-cyclotetrasiloxane and potassium hydroxide. 10 g of octamethylcyclotetrasiloxane were dissolved in 32 mls of toluene (dried over a molecular sieve). 3.785 g of dried potassium hydroxide were added and the mixture refluxed for 3 hours under a Dean and Stark apparatus until water condensation ceased.

The polymerisation mixture of hexa(trimethylsiloxy) cyclotrisiloxane and catalyst was refluxed for 3 hours under a nitrogen blanket, then allowed to stand at room temperature for 5 days. The solution appeared to be more viscous. Solid carbon dioxide was added to destroy the catalyst and the solution was washed several times with water to remove dimethyl formamide. Toluene was removed by heating on a water bath, leaving a residue of a viscous oil.

Results:
Yield of viscous oil                18.0 g

Analysis

Infra-red Spectroscopy

The Si-O absorption band had shifted from 1055 cm$^{-1}$ to 1075 cm$^{-1}$ and a shoulder at 1110 cm$^{-1}$ was no longer present. The bands at 550 cm$^{-1}$ and 785 cm$^{-1}$ were also absent. These changes suggested that the ring structure had been opened and a linear material formed.

Gas Liquid Chromatography

A comparison of peak areas before and after polymerisation showed that 88 percent of the cyclic trimer had reacted.

The product of the reaction was a linear polymeric material exhibiting a glass transition temperature of $-125°$ C., an activation energy of viscous flow of 8.3 kcal mole$^{-1}$, a molecular weight distribution of 1.14 (by Gel Permeation Chromatography) and a number average molecular weight of 1900.

EXAMPLE VII

| Materials: | |
|---|---|
| hexa(trimethylsiloxy)cyclotrisiloxane | 33.3 g |
| toluene | 25 g |
| dimethyl formamide | 10 g |
| n-butyl lithium (21 per cent in hexane) | 1 ml |

Experimental

The solvents were dried over Linde Molecular Sieve 4A before preparing the solution with pure hexa(trimethylsiloxy)cyclotrisiloxane in a 250 ml flask sealed with a 'suba-seal' rubber stopper. The 1 ml of n-butyl lithium was introduced through the rubber seal via a glass syringe and the reaction mixture allowed to stand at room temperature.

The polymerisation was monitored by analysis of the residual monomer using gas chromatography. After 2 days the reaction had proceeded to greater than 90 percent and the polymerisation was stopped by the addition of a pea of solid carbon dioxide.

The polymer was isolated from the reaction mixture by aqueous washing and solvent extraction. After removal of all traces of solvent in a vacuum oven, 28 g of polymer were left. The product was a clear viscous oil having a refractive index of 1.4082 at 20° C and a viscosity of 37 poise at 20° C.

Analysis of the polymer by gel permeation chromatography showed it to have a narrow molecular weight distribution and a molecular weight in the region of 6,000.

What is claimed is:

1. A method of producing a cyclic siloxane by silylating pseudo wollastonite with a chlorosilane characterised by reacting the pseudo wollastonite at ambient or elevated temperature with the chlorosilane in a ketone, in the presence of a minor molar proportion with respect to the chlorosilane, of a hydroxy compound soluble in the reaction medium, and purifying the resulting reaction mixture to recover the cyclic siloxane therefrom, the chlorosilane being R$_3$SiCl and the cyclic siloxane produced being of the general formula:

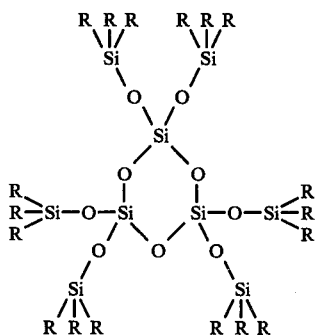

wherein the members R may differ and each R is selected from the group comprising hydrogen and the substituted and unsubstituted radicals alkyl, aryl, alkaryl and alkenyl.

2. A method according to claim 1, wherein the chlorosilane is trimethylchlorosilane and the cyclic siloxane produced is hexa(trimethylsiloxy) cyclotrisiloxane.

3. A method according to claim 1, wherein the ketone is selected from the group comprising acetone, methyl propyl ketone and cyclohexanone.

4. A method according to claim 1, wherein the hydroxy compound is selected from the group comprising water, alcohols, ether alcohols, and mixtures thereof.

5. A method according to claim 1, wherein the ketone is acetone and the hydroxy compound is tertiary butanol.

6. A method according to claim 1, wherein the minor proportion of hydroxy compound is from 0.01 to 25 mol percent based on the chlorosilane.

7. A method according to claim 1, wherein the minor proportion of hydroxy compound is from 0.1 to 16 mol percent based on the chlorosilane.

8. The method as defined in claim 1 including the further step of polymerizing the recovered cyclic siloxane in the presence of a polymerization catalyst.

9. The method of producing a cyclic siloxane intermediate product having a structure of discrete rings, which comprises the steps of:
 (a) silylating pseudo wollastonite by reacting pseudo wollastonite with a chlorosilane in a ketone which is a solvent for the chlorosilane, in the presence of a minor molar proportion with respect to the chlorosilane of a hydroxy compound soluble in the in the ketone; and
 (b) purifying the resulting reaction mixture to recover the cyclic siloxane.

10. The method as defined in claim 9 in which said wollastonite is provided by heating natural wollastonite above a temperature of about 1200° C.

11. The method as defined in claim 9 in which said pseudo wollastonite is provided by combining silica and calcium carbonate in equimolar amounts at a temperature of about 1200° C.

12. The method as defined in claim 9 in which the pseudo wollastonite is provided by preparing pure calcium silicate synthetically by precipitation from sodium silicate and calcium chloride and heating the precipitate above 1200° C.

* * * * *